US012758334B2

(12) United States Patent
Bar

(10) Patent No.: US 12,758,334 B2
(45) Date of Patent: Oct. 13, 2026

(54) METHODS AND APPARATUS FOR SURGICAL TABLE STABILIZATION

(71) Applicant: LEM Surgical AG, Bern (CH)

(72) Inventor: Yossi Bar, Muri bei Bern (CH)

(73) Assignee: LEM Surgical AG, Bern (CH)

( * ) Notice: Subject to any disclaimer, the term of this patent is extended or adjusted under 35 U.S.C. 154(b) by 169 days.

(21) Appl. No.: 18/767,753

(22) Filed: Jul. 9, 2024

(65) Prior Publication Data

US 2024/0423730 A1 Dec. 26, 2024

Related U.S. Application Data

(63) Continuation-in-part of application No. 18/734,249, filed on Jun. 5, 2024, which is a continuation of (Continued)

(51) Int. Cl.

*A61B 34/32* (2016.01)
*A61B 34/00* (2016.01)
*A61B 34/30* (2016.01)
*A61B 50/13* (2016.01)
*A61B 90/00* (2016.01)
*A61B 90/50* (2016.01)

(Continued)

(52) U.S. Cl.

CPC .............. *A61B 34/32* (2016.02); *A61B 34/25* (2016.02); *A61B 34/30* (2016.02); *A61B 50/13* (2016.02); *A61B 90/39* (2016.02); *A61B 90/50* (2016.02); *B25J 9/1682* (2013.01); *A61B 2034/2055* (2016.02); *A61B 2090/3966* (2016.02)

(58) Field of Classification Search

CPC ......... A61B 34/35; A61B 34/32; A61B 34/25; A61B 34/30; A61B 50/13; A61B 90/39; A61B 90/50; A61B 2090/508; A61B 2090/571; A61B 2034/2055; A61B 2090/3966; B25J 9/1682

USPC .............................................................. 606/1

See application file for complete search history.

(56) References Cited

U.S. PATENT DOCUMENTS 6,699,177 B1 3/2004 Wang et al.
9,125,680 B2 9/2015 Kostrzewski et al.

(Continued)

FOREIGN PATENT DOCUMENTS

CN 109549706 A 4/2019
CN 110013313 A 7/2019

(Continued)

OTHER PUBLICATIONS

PCT/EP2025/069284 International Search Report and Written Opinion dated Oct. 9, 2025.

(Continued)

*Primary Examiner* — Aaron F Roane
(74) *Attorney, Agent, or Firm* — Wilson Sonsini Goodrich & Rosati

(57) ABSTRACT

A robotic surgical system comprises a mobile cart, a first surgical robotic arm, a table support element, and a surgical robotic controller. The first surgical robotic arm is located on the mobile cart and holds a first surgical tool. The surgical robotic controller elevates the table support element to engage and to apply a controlled upward force to a structure on an underside of the surgical table to stabilize the surgical table.

31 Claims, 6 Drawing Sheets

Related U.S. Application Data application No. 18/217,595, filed on Jul. 2, 2023, now Pat. No. 12,029,511, which is a continuation of application No. PCT/IB2022/052297, filed on Mar. 14, 2022.

(60) Provisional application No. 63/253,533, filed on Oct. 7, 2021, provisional application No. 63/161,716, filed on Mar. 16, 2021.

(51) Int. Cl.
*B25J 9/16* (2006.01)
*A61B 34/20* (2016.01)

(56) References Cited

U.S. PATENT DOCUMENTS

| | | | |
|---|---|---|---|
| 10,512,509 B2 | 12/2019 | Bowling et al. | |
| 10,716,958 B2 | 7/2020 | Neff | |
| 11,638,618 B2 | 5/2023 | Schuh et al. | |
| 12,029,511 B2 | 7/2024 | Bar | |
| 12,114,946 B2 | 10/2024 | Bar et al. | |
| 2003/0074732 A1 | 4/2003 | Hanson et al. | |
| 2005/0206107 A1 | 9/2005 | Schubert et al. | |
| 2010/0286712 A1 | 11/2010 | Won et al. | |
| 2015/0193101 A1 | 7/2015 | Mannon et al. | |
| 2015/0366624 A1 | 12/2015 | Kostrzewski et al. | |
| 2018/0193101 A1 | 7/2018 | Hashimoto | |
| 2018/0360550 A1 | 12/2018 | Nakanishi | |
| 2018/0362060 A1 | 12/2018 | Schaller et al. | |
| 2019/0008598 A1 | 1/2019 | Frimer et al. | |
| 2020/0078097 A1 | 3/2020 | Gregerson et al. | |
| 2020/0268452 A1 | 8/2020 | Rezach et al. | |
| 2020/0281788 A1 | 9/2020 | Lim et al. | |
| 2020/0405432 A1* | 12/2020 | Timm | A61B 90/50 |
| 2021/0045819 A1 | 2/2021 | Castillo et al. | |
| 2021/0060767 A1 | 3/2021 | Guerrera et al. | |
| 2021/0186615 A1 | 6/2021 | Shmayahu et al. | |
| 2021/0338348 A1 | 11/2021 | Zehavi et al. | |
| 2022/0079687 A1 | 3/2022 | Sexson et al. | |
| 2022/0160445 A1 | 5/2022 | Meglan et al. | |
| 2022/0168048 A1 | 6/2022 | Shoham et al. | |
| 2022/0241032 A1 | 8/2022 | Zucker et al. | |
| 2022/0346882 A1 | 11/2022 | Zehavi et al. | |
| 2022/0395342 A1 | 12/2022 | Weiss et al. | |
| 2023/0380916 A1 | 11/2023 | Bar | |
| 2023/0414431 A1 | 12/2023 | Lim et al. | |
| 2024/0164854 A1 | 5/2024 | Bar | |
| 2024/0206973 A1 | 6/2024 | Charest et al. | |
| 2024/0261046 A1 | 8/2024 | Bar | |
| 2024/0268919 A1 | 8/2024 | Bar | |
| 2024/0341877 A1 | 10/2024 | Bar | |
| 2024/0358460 A1 | 10/2024 | Bar | |
| 2024/0366320 A1 | 11/2024 | Bar | |
| 2024/0423728 A1 | 12/2024 | Bar | |
| 2024/0423731 A1 | 12/2024 | Bar | |
| 2025/0032208 A1 | 1/2025 | Bar | |
| 2025/0049520 A1 | 2/2025 | Bar et al. | |
| 2025/0114158 A1 | 4/2025 | Bar | |
| 2025/0143813 A1 | 5/2025 | Bar | |
| 2025/0235206 A1 | 7/2025 | Bar | |
| 2025/0345127 A1 | 11/2025 | Bar et al. | |
| 2025/0345134 A1 | 11/2025 | Bar et al. | |
| 2025/0352289 A1 | 11/2025 | Bar | |
| 2026/0033901 A1 | 2/2026 | Bar | |
| 2026/0047900 A1 | 2/2026 | Bar et al. | |

FOREIGN PATENT DOCUMENTS

| | | | |
|---|---|---|---|
| CN | 111700684 A | 9/2020 |
| JP | 2017104452 A | 6/2017 |
| WO | WO-2018222470 A1 | 12/2018 |
| WO | WO-2018236594 A1 | 12/2018 |
| WO | WO-2020079596 A1 | 4/2020 |
| WO | WO-2022044009 A1 | 3/2022 |
| WO | WO-2022069993 A1 | 4/2022 |
| WO | WO-2022195460 A1 | 9/2022 |
| WO | WO-2023067415 A1 | 4/2023 |
| WO | WO-2023118984 A1 | 6/2023 |
| WO | WO-2023118985 A1 | 6/2023 |
| WO | WO-2023144602 A1 | 8/2023 |
| WO | WO-2023152561 A1 | 8/2023 |
| WO | WO-2023223215 A1 | 11/2023 |
| WO | WO-2023237922 A1 | 12/2023 |
| WO | WO-2023248005 A1 | 12/2023 |
| WO | WO-2024089473 A1 | 5/2024 |
| WO | WO-2024160875 A1 | 8/2024 |
| WO | WO-2024160896 A1 | 8/2024 |
| WO | WO-2024165397 A1 | 8/2024 |
| WO | WO-2025008416 A1 | 1/2025 |
| WO | WO-2025036864 A1 | 2/2025 |
| WO | WO-2025038127 A1 | 2/2025 |
| WO | WO-2025108905 A1 | 5/2025 |
| WO | WO-2025119761 A1 | 6/2025 |
| WO | WO-2025125379 A1 | 6/2025 |
| WO | WO-2025195791 A1 | 9/2025 |
| WO | WO-2025195902 A1 | 9/2025 |
| WO | WO-2025209993 | 10/2025 |
| WO | WO-2025257316 A1 | 12/2025 |
| WO | WO-2026012973 A1 | 1/2026 |
| WO | WO-2026012978 A1 | 1/2026 |
| WO | WO-2026062107 | 3/2026 |
| WO | WO-2026062108 | 3/2026 |

OTHER PUBLICATIONS

PCT/EP2025/069291 International Search Report and Written Opinion dated Oct. 14, 2025.
PCT/IB2022/052297 International Search Report and Written Opinion dated Jun. 14, 2022.
U.S. Appl. No. 18/217,595 Notice of Allowance dated Mar. 21, 2024.
U.S. Appl. No. 18/217,595 Office Action dated Dec. 14, 2023.
U.S. Appl. No. 18/217,595 Office Action dated Feb. 1, 2024.
U.S. Appl. No. 18/217,595 Office Action dated Sep. 28, 2023.
U.S. Appl. No. 18/734,249 Office Action dated Mar. 5, 2026.
U.S. Appl. No. 18/767,761 Office Action dated Mar. 6, 2026.
U.S. Serial No. 18/783, 197 Office Action dated Mar. 12, 2026.

* cited by examiner

METHODS AND APPARATUS FOR SURGICAL TABLE STABILIZATION

CROSS-REFERENCE TO RELATED APPLICATIONS

This application is a continuation-in-part of application Ser. No. 18/734,249, filed on Jun. 5, 2024, which is a continuation of application Ser. No. 18/217,595, filed on Jul. 2, 2023, now issued as U.S. Pat. No. 12,029,511, issued on Jun. 19, 2024, which is a continuation of PCT Application No. PCT/IB2022/052297, filed on Mar. 14, 2022, which claims the benefit of U.S. Provisional Patent Application No. 63/161,716, filed on Mar. 16, 2021, and U.S. Provisional Patent Application No. 63/253,533, filed on Oct. 7, 2021, the full disclosures of each of which are incorporated herein by reference.

BACKGROUND

Field. The disclosed technology relates generally to medical devices and methods for their use. More particularly, the technology relates to surgical robots and their deployment and use in procedures performed on patients lying on a surgical table.

Surgical robots can take a variety of forms. One common approach is to mount robotic surgical arms directly on a surgical table. A base of each arm will typically be fixed to the table, and the table and robotic system will share a common surgical coordinate space.

In another approach, which is more relevant to the disclosed technology, the robotic surgical arms are mounted on one or more mobile carts that can be moved in and out proximity with the surgical table. The robotic surgical arms will not share a common surgical coordinate space with the surgical table and, more problematically, the surgical table will not be fixed to the surgical arms and will often vibrate and shift position relative to the robotic surgical arms. Vibrations and even very small position changes can interfere with the accurate and precise control of surgical tools which is necessary for successfully performing robotic surgical procedures.

There is thus a need for robotic surgical systems which can reduce unintended movement and vibration of a surgical table during performance of a robotic surgical procedure when a patient is lying on the surgical table. It would be particularly desirable to provide mechanisms and functions which allow mobile surgical carts to stabilize an adjacent surgical bed while still allowing the position and orientation of the bed to be changed by the surgeon during the procedure. At least some if these objectives will be met by the technologies disclosed herein.

2. Background Art. Commonly owned publications and applications describing surgical robots and tools include PCT application nos. PCT/IB2022/052297 (published as WO2022/195460); PCT/IB2022/058986 (published as WO2023/067415); PCT/IB2022/058972 (published as WO2023/118984); PCT/IB2022/058982 (published as WO2023/118985); PCT/IB2022/058978 (published as WO2023/144602); PCT/IB2022/058980 (published as WO2023/152561); PCT/IB2023/055047 (published as WO2023/223215); PCT/IB2022/058988 (published as WO2023/237922); PCT/IB2023/055439; PCT/IB2023/055662; PCT/EP2024/052338; PCT/IB2023/055663; PCT/EP2024/052338; PCT/IB2023/056911; PCT/EP2024/052353; and U.S. provisional application Nos. 63/532,753, 63/568,102, 63/578,395; 63/606,001; 63/609,490; 63/615,076; 63/634,161, the full disclosures of each of which are incorporated herein by reference.

SUMMARY

In a first aspect, the disclosed technology provides a method for performing robotic surgery on a patient lying on a surgical table. The method comprises positioning a robotic surgical cart adjacent to the surgical table. A table support element disposed on the robotic surgical cart is elevated to engage and to apply a controlled upward force to a structure on an underside of the surgical table to stabilize the surgical table. A surgical procedure can then be performed on the patient using one or more tools moved by at least one surgical robotic arm located on the mobile surgical robotic cart while said surgical table remains stabilized by the table support element. In this way, vibrations and unintended movement of the table relative to the robotic surgical cart can be reduced or eliminated.

In some instances, the methods may further comprise positioning the robotic surgical cart beneath the surgical table, where the table support element is then elevated from an upper surface of the robotic surgical cart to engage the underside of the surgical table.

In other instances, the methods may further comprise positioning the robotic surgical cart adjacent to the surgical table, where the table support element may be extended laterally from the robotic surgical cart and then used to elevate and engage the underside of the surgical table.

In some instances, the controlled upward force may be in a range from 50 N (5 kgf) to 500 N (50 kgf). For example, the table support element may be driven by a table support element driver, and the table support element driver controlled to maintain an upward force at a set point in the range. Typically, such controlling may comprise measuring the actual upward force and adjusting an output of the table support element driver to maintain the measured upward force at the set point.

In some instances, the table support element may comprise a bar that extends laterally across the robotic surgical cart.

In other instances, the table support element may comprise a plate having an upper surface that is generally parallel to an upper surface of the robotic surgical cart.

In some instances, these methods may further comprise repositioning the surgical table during the robotic surgery, where a robotic surgical controller adjusts a position of the table support element to maintain the controlled upward force in a desired range.

In some instances, adjusting the position of the table support element comprises controlling a table support element driver with a robotic surgery controller disposed om the mobile surgical robotic cart.

In a second aspect, the disclosed technology provides robotic surgical systems configured to perform robotic surgery on a patient lying on a surgical table. Such robotic surgical systems typically comprise a mobile cart, a first surgical robotic arm, a table support element, and a surgical robotic controller. The first surgical robotic arm is disposed on the mobile cart and is configured to hold a first surgical tool, and the surgical robotic controller is configured to (a) kinematically position the first robotic arms in a surgical robotic coordinate space and (b) elevate the table support element to engage and to apply a controlled upward force to a structure on an underside of the surgical table to stabilize the surgical table.

In some instances, the table support element is located on an upper surface of the mobile cart and is configured to apply the controlled upward force to the structure on the underside of the surgical table when the mobile cart chassis is positioned beneath the surgical table. In some cases, the table support element is located in a recessed region on the upper surface of the mobile cart.

In other instances, the table support element is configured to extend laterally from the mobile cart and to engage the underside of the surgical table when the mobile cart is positioned adjacent to the surgical table.

In some instances, the surgical robotic controller is configured to control the upward force in a range from 50 N (5 kgf) to 500 N (50 kgf).

In some instances, the robotic surgical systems may further comprise a support element driver, wherein the surgical robotic controller is configured to control the support element driver to maintain the upward force at a set point in said range. For example, the support element driver may comprise any one or more of a rack-and-pinon gear, a continuous-loop chain, a servo-controlled motor drive, and a fluidic piston, and the support element may comprises a bar, a plate, or any other structure or assembly that has a surface configured to engage a structure on the underside of the bed and sufficient structural strength to transmit the desired support force. In a specific instance, controlling the upward force applied by the table support element to the structure on the underside of the surgical table may comprise measuring an actual upward force and adjusting an output of the table support element driver to maintain the measured upward force at the set point.

In some instances, the surgical robotic systems may further comprise at least a second surgical robotic arm disposed on the mobile cart and configured to hold a second surgical tool.

In some instances, the surgical robotic systems may further comprise a display/controller interface disposed on the mobile cart.

In a third aspect, the disclosed technology provides a method for performing robotic surgery on a patient lying on a surgical table The method comprises positioning a mobile surgical robotic chassis beneath the surgical table. An element on the chassis is pressed upwardly against a bottom of the bed to stabilize the surgical table, and a surgical procedure is performed on the patient using one or more tools moved by surgical robotic arms located on the mobile surgical robotic chassis while said mobile surgical robotic chassis remains stabilized by the element.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

With reference now to the figures and several representative embodiments of the described technology, the following detailed description is provided.

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Figure 1:
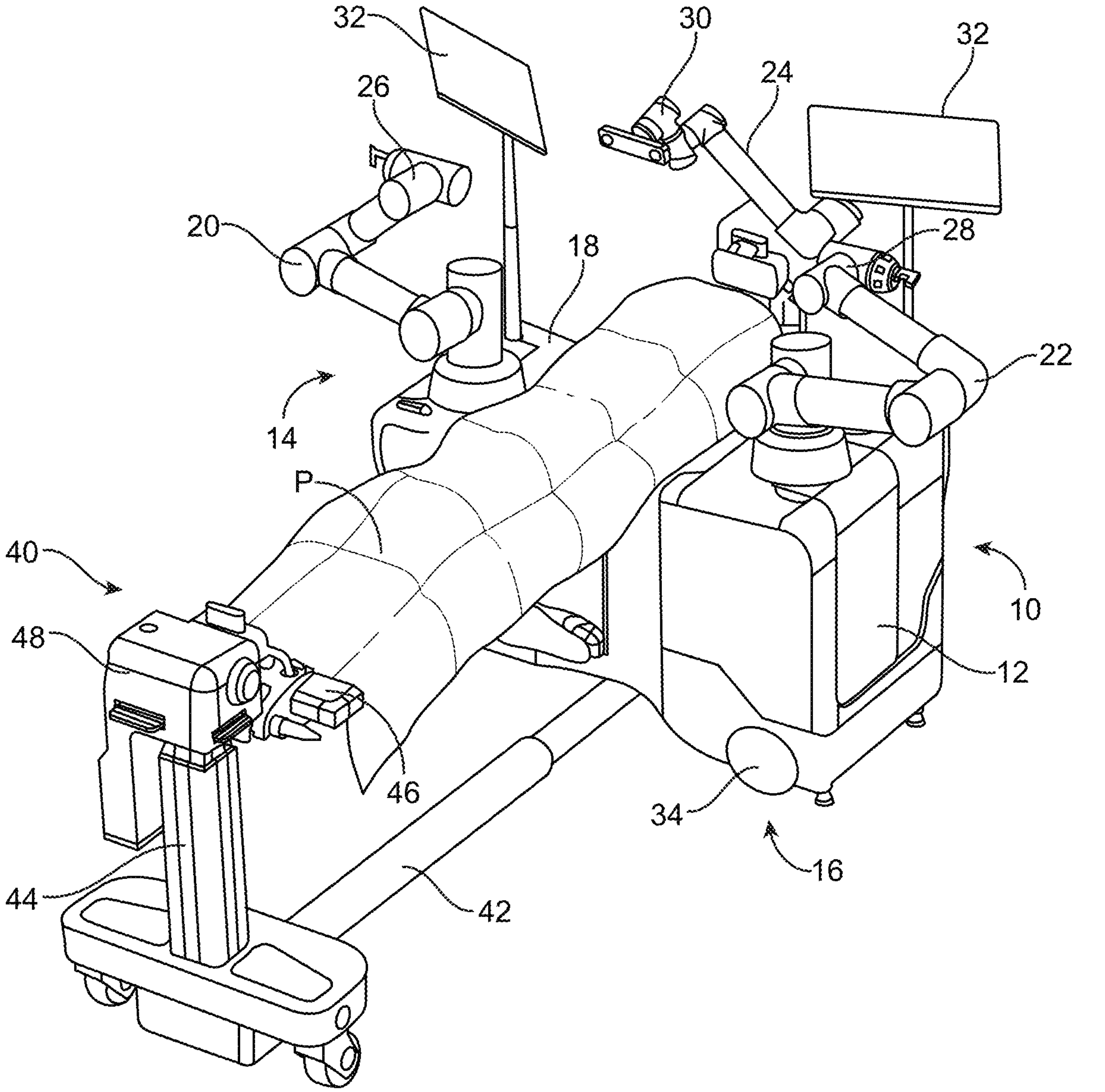
FIG. 1 is a perspective view of a mobile surgical robotic cart of the disclosed technology shown positioned beneath a surgical table with surgical robotic arms deployed over a draped patient, in accordance with some embodiments.

An exemplary robotic surgical system 10 incorporating the disclosed technologies and intended particularly for use in the methods described and claimed herein is shown in FIG. 1. The robotic surgical system 10 can comprise a chassis 12, typically a single, rigid frame which may provide a base or platform for three robotic arms 20, 22 and 24 that are placed relatively far apart on opposite longitudinal ends 14 and 16 of an upper surface 18 of the chassis 12, typically approximately one meter apart, thus allowing for desirable attributes such as reachability, maneuverability, and an ability to apply significant force. In the illustrated embodiment, robotic surgical arms 20 and 22 are on the first end 14 of the chassis 12 and robotic surgical arm 22 is on the second end 16 of the chassis. The chassis can be mobile, e.g., being in the form of a mobile cart as described in commonly owned PCT/IB2022/052297 (published as WO2022/195460), previously incorporated herein by reference. In other embodiments and implementations, the surgical arms 20, 22 and 24 can be mounted on a base or other structure of a surgical table. For performing tool alignment in accordance with the disclosed technology, it necessary only that the robotic surgical arms be located on a stable platform that allows the arms to be moved kinematically or otherwise within a common robotic coordinate system under the control of a surgical robotic controller, typically an on-board controller have a user interface, such as display screen 32.

The single, rigid chassis of the disclosed technology can include a single mobile cart, as disclosed for example in commonly owned PCT/IB2022/052297 (published as WO2022/195460), the full disclosure of which has been previously incorporated herein by reference. In other instances, however, the single, rigid chassis may comprise separate modules, platforms, or components, that are assembled at or near the surgical table, as described for example in commonly owned PCT Application no. PCT/EP2024/052353, entitled Integrated Multi-Arm Mobile Surgical Robotic System, filed on Jan. 29, 2024, the full disclosure of which is incorporated herein by reference. The only requirement of the single, rigid chassis is that it provide a stable base for all the surgical arms so that they may be accurately and precisely kinematically positioned and tracked by the surgical robotic controller in a single surgical robotic coordinate space.

The chassis 12 of the robotic surgical system 10 can be configured to be temporarily placed under a surgical table 40 when performing the robotic surgical procedure, allowing the robotic surgical system 10 to be stored remotely before and after the procedure. The robotic arms 20, 22, and 24 may optionally be configured to be retracted into the chassis 12 of the robotic surgical system, allowing the system to be moved into or out of the surgical field in a compact configuration. The first and second robotic arms 20 and 22 are shown to hold tool holders 26 and 28 as described for example in commonly owned PCT application no. PCT/EP2024/068766, filed on Jul. 4, 2024, the full disclosure of which is incorporated herein by reference. The first and second robotic arms 20 and 22 can be configured to hold tool grippers, such as those described in U.S. patent application Ser. No. 18/631,921, the full disclosure of which is incorporated herein by reference, or any one of a variety of robotic surgical tools known in the art. The chassis 12 can be mounted on wheels 42, casters, rollers, or the like, to allow repositioning the cassis within the operating room and/or beneath the surgical table 40.

In other disclosed embodiments of the present technologies, the surgical robotic chasses may be designed to be located adjacent to the surgical tables and in some cases may not be able to be placed underneath the table. See, e.g., FIGS. 7A, 7B, 8A, and 8B which describe such alternatives.

The surgical table 40 can comprise a mobile frame 42 having support columns 44 at the head and foot ends of the table (only the support column at the foot end is visible in FIG. 1). A patient bed 46 for supporting draped patient P spans the axial length of the surgical table 40 and is attached to the support columns 44 by bed adjustment mechanisms 48. The support columns 44 can be vertically adjustable, allowing the height of each end of the patient bed 46 to be independently changed, and the bed adjustment mechanism 48 can allow the patient bed 46 to be reoriented about one or several axes. The column heights and/or the patient bed orientation can often be changed many times during a single patent procedure.

Figure 2:
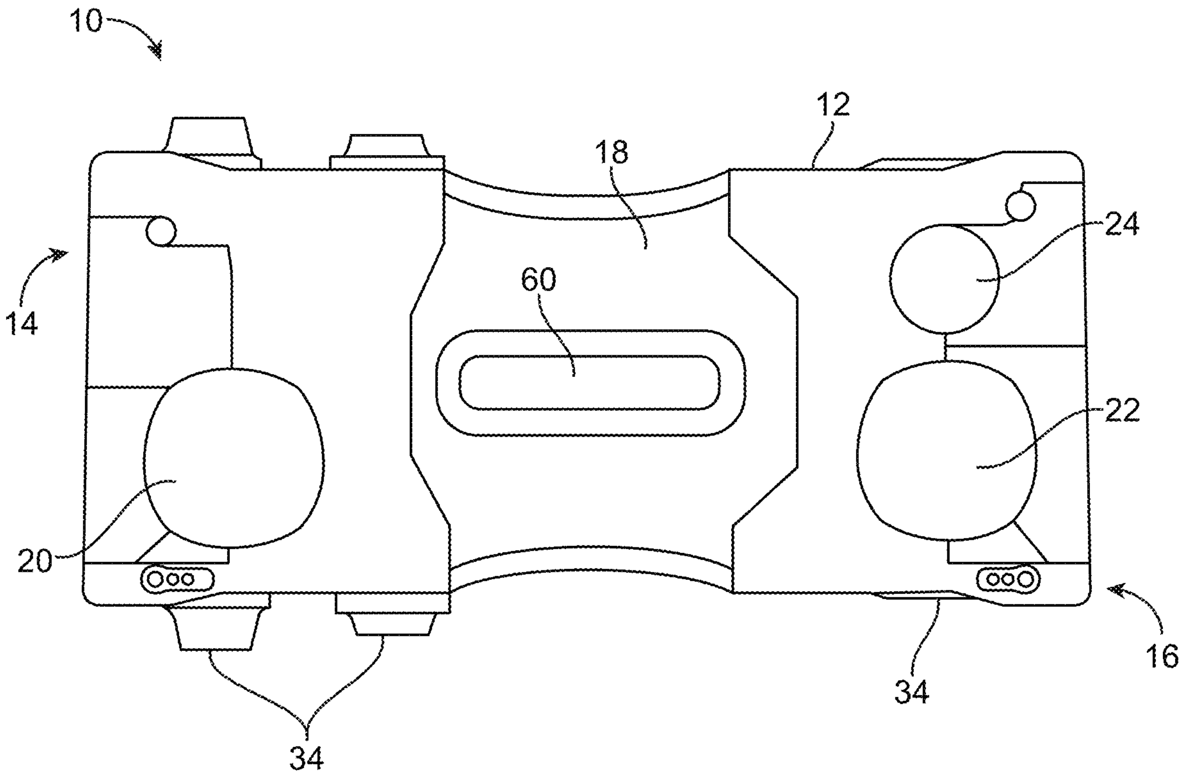
FIG. 2 is a top view of the mobile surgical robotic cart of FIG. 1 showing the location of a table support element of the disclosed technology, in accordance with some embodiments.
Figure 3:
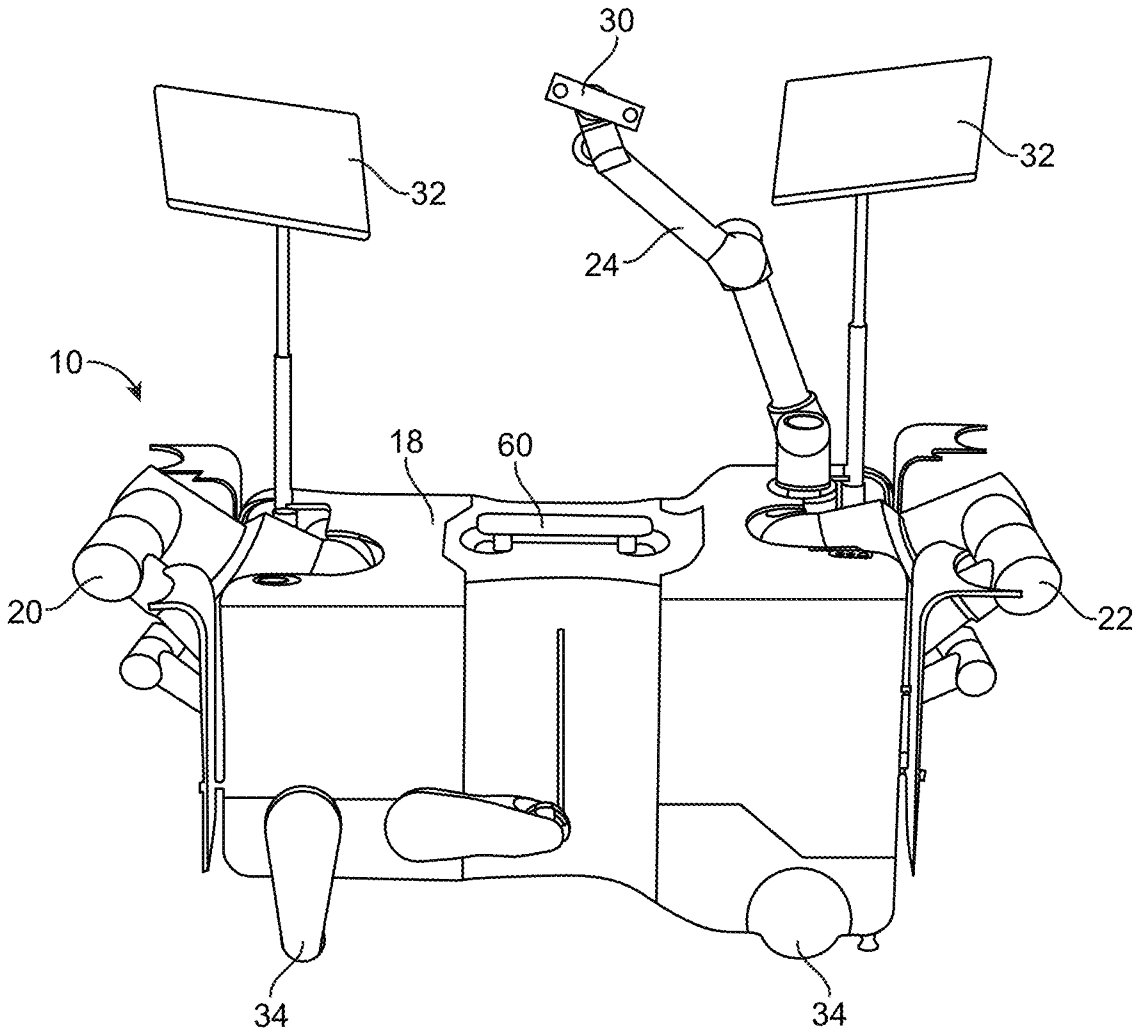
FIG. 3 is a perspective view of the mobile surgical robotic cart of FIG. 1 showing the table support element of the disclosed technology in a partially raised position, in accordance with some embodiments.

Referring now to FIGS. 2 and 3, the robotic surgical system 10 can include a table support element 60, illustrated as a flat plate but which could have a variety of designs, which can be raised from a lowered position as shown in FIG. 2 to a raised position as shown in FIG. 3. The support element 60 may initially lie flat over (or is recessed into) the upper surface 18 of the chassis 12 and can be deployed to press up against the bottom of the surgical table when the cart is deployed under the table, stabilizing the surgical table even when patient movement is taken into account and/or external forces are applied to the patient or table.

Figure 4A:
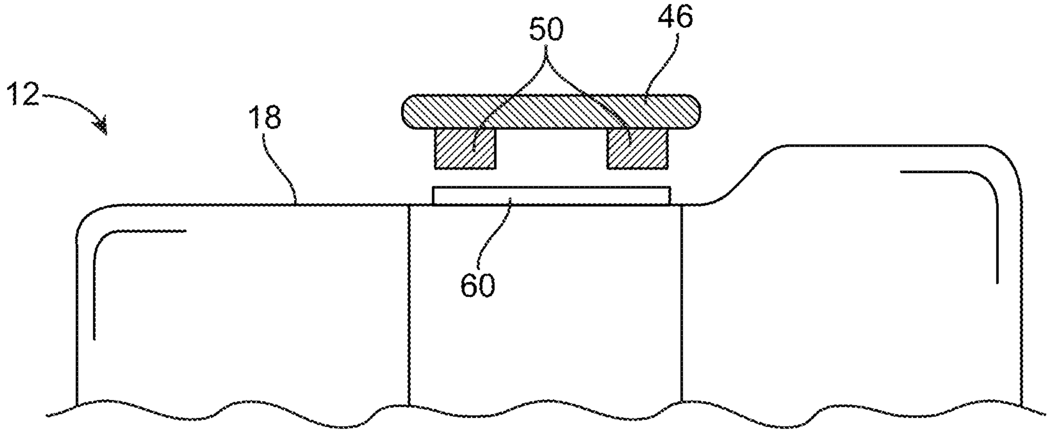
FIGS. 4A to 4C are schematic illustrations of the table support element of the disclosed technology being elevated to support a surgical table in accordance with the methods disclosed herein, in accordance with some embodiments.
Figure 4B:
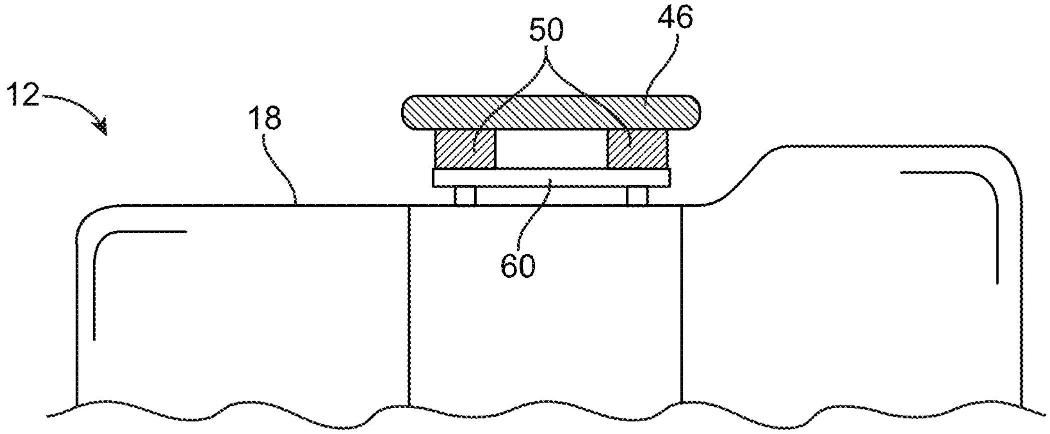

As shown in FIG. 4A, the table support element 60 can be in its initial or pre-deployed position lying flat on the upper surface 18 of the chassis 12. The patient bed 46 can be positioned above the table support 60 with frame struts 50 spaced above the table support by a distance of several to tens of centimeters. When in the unsupported position, as shown in FIG. 4A, the patient bed 46 can be unstable and subject to vibrations and unintended movements which can be a particular challenge in bone drilling and other orthopedic procedures that require significant forces to be applied to the patient's bony anatomy.

Figure 4C:
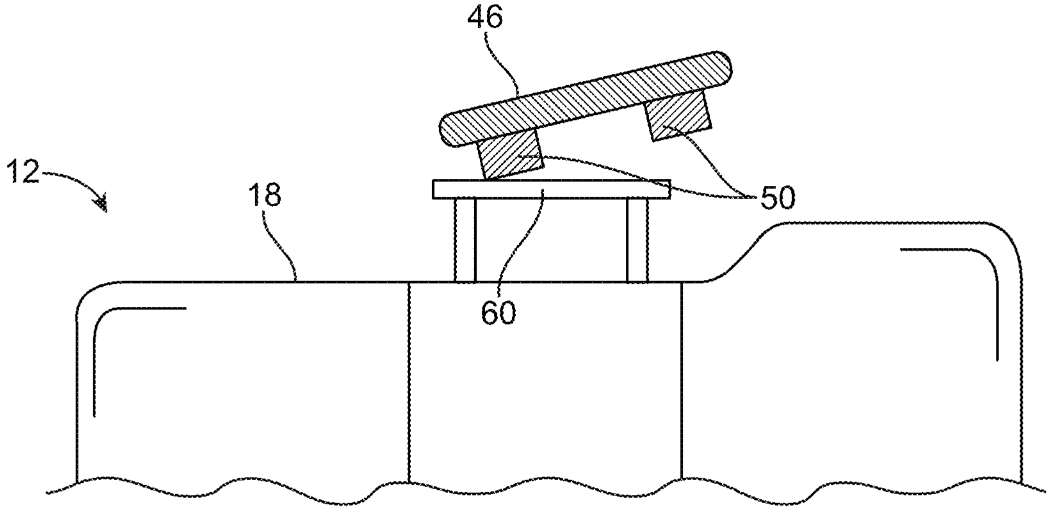

In order to stabilize the patient bed 46, the table support 60 can be raised so that its upper surface contacts an underside of the patient bed 46, for example engaging one or more frame struts 50. As shown in FIG. 4A, the patient bed may not be tilted, and table support 60 can engage each of two frame struts 50. In contrast, as shown in FIG. 4C, the patient bed 46 can be tiled about its longitudinal axis and the table support can engage only one of the of two frame struts 50. Engaging the table support element 60 with only a single point or line on the underside of the surgical bed can provide a significant degree of stability.

In operation, the table support element 60 can be elevated with a table support driver configured to apply an upward biasing force, typically controlled with a set point in a range from 50 N (5 kgf) to 500 N (50 kgf). For example, the table support driver may be configured to move upward until it encounters the underside of the patient bed which provides a resistance equal to the set point. Motion of the table support element can then stop (the upward and downward forces will be balanced), but the table support element can continue to apply the biassing force which inhibits vibrations and unintended movement of the patient bed.

The table support driver can cause the table support member 60 to follow all major as well as minor movements of the table to the extent they do occur. While the table support member can suppress many minor movements resulting from patient movement and other perturbances, those which do occur will be lessened and the table support member can be elevated or dressed in order to follow such table movement. The table support driver can also cause the table support member to follow larger patient bed movements resulting from the surgeon intentionally repositioning the patient bed as required be y a particular procedure.

Figure 5A:
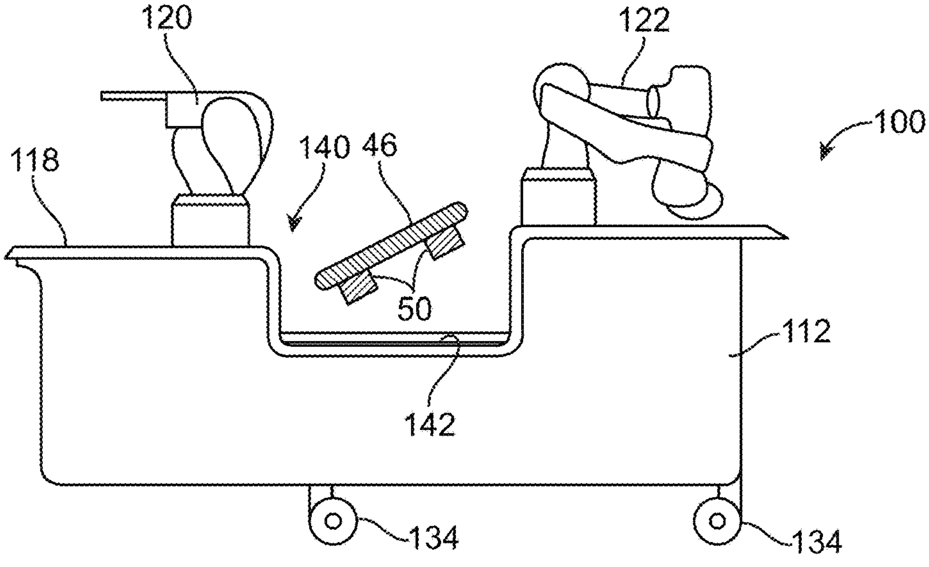
FIGS. 5A and 5B are side views of an alternative embodiment of a mobile surgical robotic cart of the disclosed technology shown positioned beneath a surgical table with a table support element in a lowered position (FIG. 5A) and a raised position supporting the surgical table (FIG. 5B), in accordance with some embodiments.
Figure 5B:
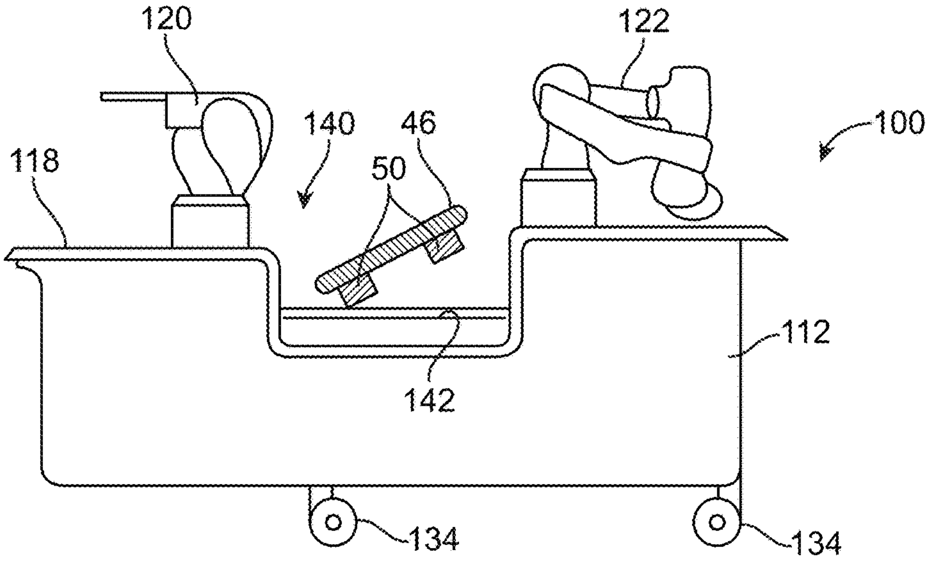

Referring now to FIGS. 5A and 5B, the design of a second robotic surgical system 100 will be described. The robotic surgical system 100 can comprise a chassis 112 having an upper surface 118, first and second robotic surgical arms 120 and 122, respectively, and wheels 134. To this extent, the second robotic surgical system 100 is similar if not identical to the first robotic surgical system 10. The primary difference is that the table support member can comprise a table support bar 142 disposed in a recessed region 140 formed in the upper surface 118 of the chassis 112.

Typically, the patient bed 46 of a surgical table can be received in the recessed region 140 of the formed in the upper surface 118 of the chassis 112, as shown in FIGS. 5A and 5B. In FIG. 5A, the upper surface of the table support bar 142 is located below the table support bar 46 which is placed in the recessed region 140. As shown in FIG. 5B, the table support bar 142 is raised by the table support driver to engages the lowermost frame strut 50 and provide stabilization as discussed above.

Figure 6:
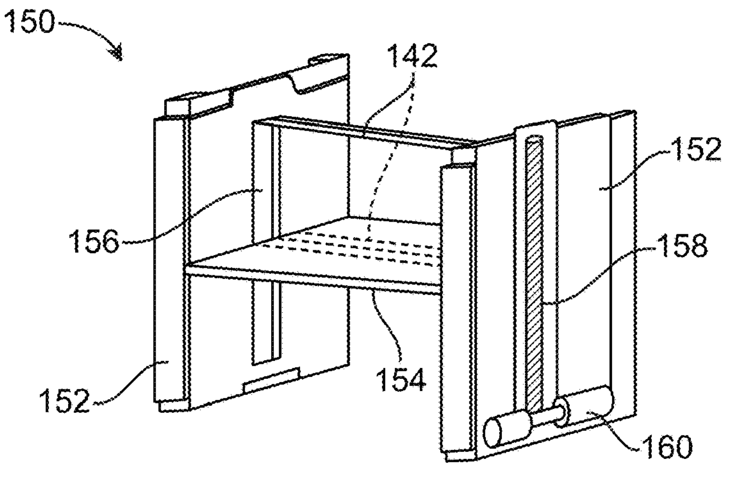
FIG. 6 is an isolated view of the table support assembly of FIGS. 5A and 5B including a table support driver, in accordance with some embodiments.

Details of an exemplary table support assembly 150 of the robotic surgical system 100 are shown in FIG. 6. Side walls 152 may define opposed sides of the recessed region 140 and be disposed on opposite sides of a bottom plate 154. The table support bar 142 can travel upwardly and downwardly in tracks 156 formed on the each of the opposed sides and is raised and lowered by a vertical driver, such as a rack-and-pinion gear 158, driven by a motor 160. Raising and lowering of the table support bar 142 can be controlled by the robotic controller to maintain a constant force against the underside to the patient bed 46 even as the bed changes positions (intentionally or unintentionally) within the recessed region 140.

Figure 7A:
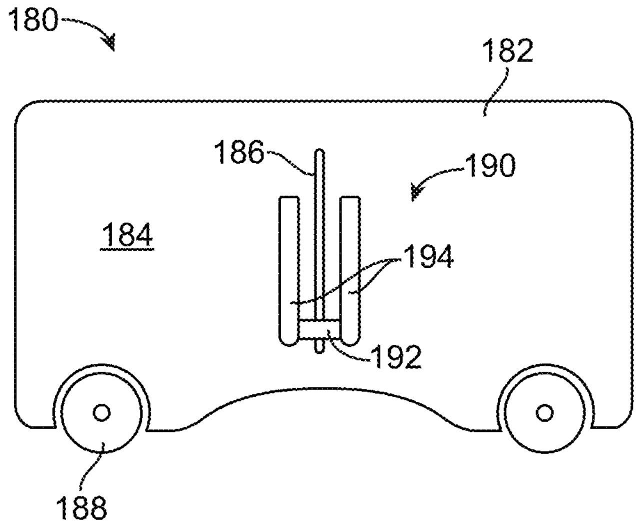
FIGS. 7A and 7B are side and front views, respectively, of another alternative mobile surgical robotic cart having a laterally deployable table support element of the disclosed technology in accordance with the principles of the disclosed technology, in accordance with some embodiments.
Figure 7B:
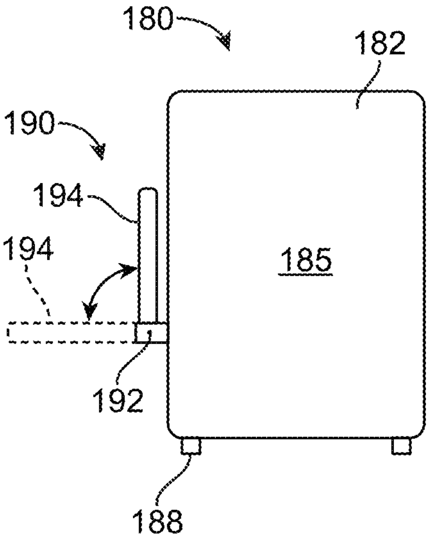

As discussed to this point, the table support mechanisms can be deployed from an upper surface of a surgical robotic chassis disposed beneath a patient bed of a surgical table. In contrast, robotic carts of the disclosed technologies may incorporate table support elements located on a side of a robotic surgical chassis to deployed laterally and to be used with a surgical bed located adjacent to the robotic chassis. For example, a robotic surgical system 180 can comprise a chassis 182 having a side 184 and a first end 185, as shown in FIGS. 7A and 7B, respectively. The chassis can have a slot 186 formed in the side 184 and include wheels 188 on the bottom. A table support assembly 190 includes a sliding block 192 having folding supports 194 attached thereto. The sliding block 192 can be configured to travel up and down in the slot 186 driven by a table support driver (not shown). The folding supports 194 may be folded upwardly, as shown in full line in FIG. 7B for storage, and folded downwardly, as shown in broken line in FIG. 7B, when in use.

Figure 8A:
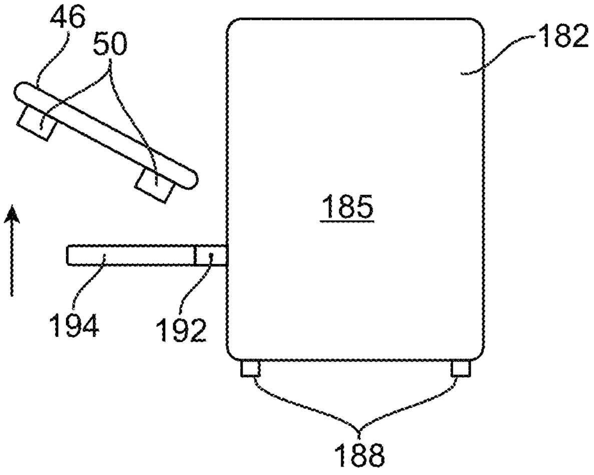
FIGS. 8A and 8B are schematic illustrations of the table support element of FIGS. 7A and 7B being elevated to support a surgical table in accordance with the methods disclosed herein, in accordance with some embodiments.
Figure 8B:
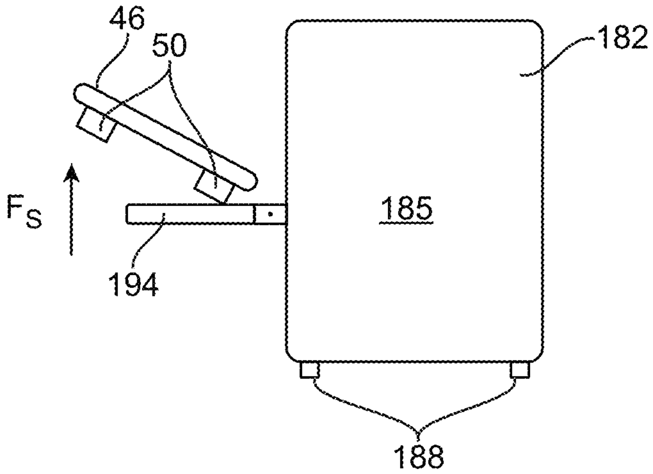

As shown in FIG. 8A, the surgical robotic chassis 182 may be positioned adjacent to the surgical bed 46 of a surgical table 100 (FIG. 1) at the beginning of a procedure. After deploying the folding supports 194, the table support driver can be actuated to raise the sliding block 192 with a controlled force, as previously described. The folding supports 194 can be elevated until the engage a lowermost point on the underside of the patient bed 46, e.g., frame strut 50 as shown in FIG. 8B. The force can then be maintained throughout the robotic procedure in order to at least partially stabilize the patient bed 46.

REFERENCE NOS

10 Robotic surgical system
12 Chassis
14 First end
16 Second end
18 Upper Surface
20 Robotic surgical arm (first)
22 Robotic surgical arm (second)
24 Robotic surgical arm (third)
26 First gripper
28 Second gripper
30 Navigation camera
32 Display/Controller
34 Wheel
40 Surgical table
42 Mobile frame
44 Support column
46 Patient bed
48 Bed adjustment mechanism
50 Frame strut
60 Table support element
100 Robotic surgical system
112 Chassis
118 Upper surface
120 Robotic surgical arm (first)
122 Robotic surgical arm (second)
134 Wheel
140 Recessed region
142 Table support bar
150 Table support assembly
152 Side walls
154 Bottom plate
156 Tracks
158 Vertical drive
160 Drive motor
180 Robotic surgical system
182 Chassis
184 Side
185 First end
186 Slot
188 Wheels
190 Table support assembly
192 Sliding block
194 Folding supports While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. One of skill in the art will realize that several variations on the disclosed embodiments are possible while staying within the bounds of the disclosed technology. Solely by way of example, different variations in the number of navigation cameras, robotic arms, markers and end effectors can be used without departing from the described technology. As another example, markers of varying sizes can be used. The embodiments provided are representative in nature.

What is claimed is:

1. A method for performing robotic surgery on a patient lying on a surgical table, the method comprising:

positioning a robotic surgical cart adjacent to the surgical table;

elevating a table support element disposed on the robotic surgical cart to engage and to apply a controlled upward force to a structure on an underside of the surgical table to stabilize the surgical table;

performing a surgical procedure on the patient using one or more tools moved by at least one surgical robotic arm located on the mobile surgical robotic cart while the surgical table remains stabilized by the table support element;

wherein the controlled upward force is in a range from 50 N (5 kgf) to 500 N (50 kgf).

2. The method of claim 1, further comprising positioning the robotic surgical cart beneath the surgical table, wherein the table support element is elevated from an upper surface of the robotic surgical cart to engage the underside of the surgical table.

3. The method of claim 1, further comprising positioning the robotic surgical cart adjacent to the surgical table, wherein the table support element is extended laterally from the robotic surgical cart and then elevated to engage the underside of the surgical table.

4. The method of claim 1, wherein the table support element is driven by a table support element driver, further comprising controlling the table support element driver to maintain an upward force at a set point in the range.

5. The method of claim 4, wherein controlling comprises measuring the actual upward force and adjusting an output of the table support element driver to maintain the measured upward force at the set point.

6. The method of claim 1, wherein the table support element comprises a bar that extends laterally across the robotic surgical cart.

7. The method of claim 1, wherein the table support element comprises a plate having an upper surface that is generally parallel to an upper surface of the robotic surgical cart.

8. The method of claim 1, further comprising repositioning the surgical table during the robotic surgery, wherein a robotic surgical controller adjusts a position of the table support element to maintain the controlled upward force in a desired range.

9. The method of claim 1, wherein adjusting the position of the table support element comprises controlling a table support element driver with a robotic surgery controller disposed om the mobile surgical robotic cart.

10. A robotic surgical system configured to perform robotic surgery on a patient lying on a surgical table, the robotic surgical system comprising:

a mobile cart;

a first surgical robotic arm disposed on the chassis and configured to hold a first surgical tool;

a table support element; and a surgical robotic controller, wherein the surgical robotic controller is configured to (a) kinematically position the first robotic arms in a surgical robotic coordinate space and (b) elevate the table support element to engage and to apply a controlled upward force to a structure on an underside of the surgical table within a range to stabilize the surgical table; and a table support element driver, wherein the surgical robotic controller is configured to control the table support element driver to maintain the upward force at a set point in the range.

11. The robotic surgical system of claim 10, wherein the table support element is located on an upper surface of the mobile cart and configured to apply the controlled upward force to the structure on the underside of the surgical table when the mobile cart chassis is positioned beneath the surgical table.

12. The robotic surgical system of claim 10, wherein the table support element is located in a recessed region on the upper surface of the mobile cart.

13. The robotic surgical system of claim 10, wherein the table support element is configured to extend laterally from the mobile cart and to engage the underside of the surgical table when the mobile cart is positioned adjacent to the surgical table.

14. The robotic surgical system of claim 10, wherein the surgical robotic controller is configured to control the upward force in a range from 50 N (5 kgf) to 500 N (50 kgf).

15. The robotic surgical system of claim 10, wherein the table support element driver comprises any one or more of a rack-and-pinon gear, a continuous-loop chain, a servo-controlled motor drive, and a fluidic piston.

16. The robotic surgical system of claim 15, wherein the table support element comprises a bar.

17. The robotic surgical system of claim 15, wherein the table support element comprises a plate.

18. The robotic surgical system of claim 10, wherein controlling the upward force applied by the table support element to the structure on the underside of the surgical table comprises measuring an actual upward force and adjusting an output of the table support element driver to maintain the measured upward force at the set point.

19. The robotic surgical system of claim 10, further comprising at least a second surgical robotic arm disposed on the mobile cart and configured to hold a second surgical tool.

20. The robotic surgical system of claim 10, further comprising a display/controller interface disposed on the mobile cart.

21. A robotic surgical system configured to perform robotic surgery on a patient lying on a surgical table, the robotic surgical system comprising:

a mobile cart;

a first surgical robotic arm disposed on the chassis and configured to hold a first surgical tool;

a table support element;

a surgical robotic controller, wherein the surgical robotic controller is configured to (a) kinematically position the first robotic arms in a surgical robotic coordinate space and (b) elevate the table support element to engage and to apply a controlled upward force to a structure on an underside of the surgical table to stabilize the surgical table; and a display/controller interface disposed on the mobile cart.

22. The robotic surgical system of claim 21, wherein the table support element is located on an upper surface of the mobile cart and configured to apply the controlled upward force to the structure on the underside of the surgical table when the mobile cart chassis is positioned beneath the surgical table.

23. The robotic surgical system of claim 21, wherein the table support element is located in a recessed region on the upper surface of the mobile cart.

24. The robotic surgical system of claim 21, wherein the table support element is configured to extend laterally from the mobile cart and to engage the underside of the surgical table when the mobile cart is positioned adjacent to the surgical table.

25. The robotic surgical system of claim 21, wherein the surgical robotic controller is configured to control the upward force in a range from 50 N (5 kgf) to 500 N (50 kgf).

26. The robotic surgical system of claim 21, further comprising a table support element driver, wherein the surgical robotic controller is configured to control the table support element driver to maintain the upward force at a set point in the range.

27. The robotic surgical system of claim 26, wherein the table support element driver comprises any one or more of a rack-and-pinon gear, a continuous-loop chain, a servo-controlled motor drive, and a fluidic piston.

28. The robotic surgical system of claim 27, wherein the table support element comprises a bar.

29. The robotic surgical system of claim 28, wherein the table support element comprises a plate.

30. The robotic surgical system of claim 26, wherein controlling the upward force applied by the table support element to the structure on the underside of the surgical table comprises measuring an actual upward force and adjusting an output of the table support element driver to maintain the measured upward force at the set point.

31. The robotic surgical system of claim 21, further comprising at least a second surgical robotic arm disposed on the mobile cart and configured to hold a second surgical tool.

* * * * *